(12) United States Patent
Wang

(10) Patent No.: US 11,491,298 B1
(45) Date of Patent: Nov. 8, 2022

(54) AIR HUMIDIFICATION DEVICE AND HUMIDIFICATION SYSTEM

(71) Applicant: Telesair, Inc., Irvine, CA (US)

(72) Inventor: Qing Wang, Palo Alto, CA (US)

(73) Assignee: TELESAIR, INC., Irvine, CA (US)

( * ) Notice: Subject to any disclaimer, the term of this patent is extended or adjusted under 35 U.S.C. 154(b) by 0 days.

(21) Appl. No.: 17/564,897

(22) Filed: Dec. 29, 2021

Related U.S. Application Data

(60) Provisional application No. 63/211,427, filed on Jun. 16, 2021.

(51) Int. Cl.
*A61M 16/16* (2006.01)
*A61M 16/10* (2006.01)

(52) U.S. Cl.
CPC ........ *A61M 16/161* (2014.02); *A61M 16/109* (2014.02); *A61M 2205/3368* (2013.01)

(58) Field of Classification Search
CPC . A61F 2007/0061; A61F 7/12; A61M 11/041; A61M 11/042; A61M 13/003; A61M 13/006; A61M 16/0051; A61M 16/0066; A61M 16/024; A61M 16/026; A61M 16/0666; A61M 16/0875; A61M 16/0891; A61M 16/101; A61M 16/105; A61M 16/1065; A61M 16/1075; A61M 16/109; A61M 16/1095; A61M 16/12; A61M 16/142; A61M 16/16; A61M 16/161; A61M 16/162; A61M 16/20; A61M 2016/0027; A61M 2016/0033; A61M 2016/0039; A61M 2202/0208; A61M 2202/0225; A61M 2202/0241; A61M 2202/025; A61M 2202/0266; A61M 2202/0283; A61M 2205/02; A61M 2205/12; A61M 2205/123; A61M 2205/127; A61M 2205/18; A61M 2205/3317; A61M 2205/3331; A61M 2205/3334; A61M 2205/3337; A61M 2205/3365; A61M 2205/3368; A61M 2205/3375; A61M 2205/3569; A61M 2205/3653; A61M 2205/50; A61M 2205/505; A61M 2205/584;
(Continued)

(56) References Cited

U.S. PATENT DOCUMENTS 5,368,786 A * 11/1994 Dinauer .................... F24F 3/14
 261/130
10,982,910 B2 * 4/2021 Kolb ...................... B01J 20/103
(Continued)

*Primary Examiner* — Annette Dixon
(74) *Attorney, Agent, or Firm* — Maier & Maier, PLLC

(57) ABSTRACT

Provided are a humidification device and a humidification system, the humidification device includes a desorption structure, where the desorption structure includes a first housing, a heating layer and a desorption metal organic framework (MOF) portion; the first housing is provided with an air inlet and an air outlet; the heating layer is arranged in an inner side of the first housing; the desorption MOF portion is arranged inside the first housing and attached to the heating layer, where a temperature of the desorption MOF portion is adjusted based on a temperature of the heating layer, and the desorption MOF portion is of a preset moisture. The humidification device provided by the present disclosure can realize precise control on the humidity of the air, and have the properties of ease of use, high capacity, portability and low cost.

8 Claims, 3 Drawing Sheets

(58) Field of Classification Search
CPC ...... A61M 2205/75; A61M 2205/8206; A61M 2205/8231; A61M 2205/8237; A61M 2206/14; A61M 2230/005; A61M 2230/205; A61M 2230/432; B01D 2253/102; B01D 2253/104; B01D 2253/106; B01D 2253/108; B01D 2253/204; B01D 2253/34; B01D 2253/342; B01D 2255/1021; B01D 2255/1023; B01D 2255/1025; B01D 2255/20761; B01D 2258/06; B01D 2259/4508; B01D 53/0407; B01D 53/0454; B01D 53/0462; B01D 53/261; B01D 53/268; B01J 20/103; B01J 20/18; B01J 20/20; B01J 20/226; B01J 20/28042; B01J 20/28047; B01J 20/3204; B01J 20/3206; B01J 20/3236; B01J 20/3238; B01J 20/324; B01J 20/3433; B01J 20/3483; B01J 7/00; F17C 11/00; F17C 2201/0138; F17C 2250/03; F17C 2270/025; F17C 5/00; F24F 12/006; F24F 2003/1435; F24F 3/14; F24F 3/1411; F25B 17/08; F25B 2315/005; F25B 37/00; F28D 21/0014; F28F 27/00; G05D 22/02; G05D 23/1931; G05D 23/22; Y02A 30/27; Y02B 30/56; Y02C 20/10
See application file for complete search history.

(56) References Cited

U.S. PATENT DOCUMENTS

| | | | |
|---|---|---|---|
| 2009/0110379 A1* | 4/2009 | McGhin | A61M 16/1095 392/485 |
| 2015/0367087 A1* | 12/2015 | Dor Zidon | A61M 13/003 604/26 |
| 2017/0203073 A1* | 7/2017 | Dor-Zidon | A61M 16/024 |
| 2018/0328601 A1* | 11/2018 | Weickert | F24F 12/006 |
| 2019/0209801 A1* | 7/2019 | Kimble | A61M 16/16 |

* cited by examiner

AIR HUMIDIFICATION DEVICE AND HUMIDIFICATION SYSTEM

CROSS-REFERENCE TO RELATED APPLICATIONS

This application claims priority to U.S. Provisional Application No. 63/211,427, filed on Jun. 16, 2021, the disclosure of which is hereby incorporated by reference in its entity.

TECHNICAL FIELD

The present disclosure relates generally to the technical field of devices for humidification and, in particular, to a humidification device and a humidification system.

BACKGROUND

A respiratory disease may be caused by viruses, for example, the COVID-19 virus. Such respiratory disease may result in sever impacts in people's daily life. Chronic obstructive pulmonary disease (COPD), as a progressive life threatening lung disease, is given a lot of attention in the current COVID-19 pandemic.

Artificial respiratory system is required to effectively treat patients with respiratory diseases such as COPD. Respiratory conditioning, in particular respiratory humidification is a crucial element of the artificial respiratory system.

This background information is provided to reveal information believed by the applicant to be of possible relevance to the present disclosure. No admission is necessarily intended, nor should be construed, that any of the preceding information constitutes prior art against the present disclosure.

SUMMARY

The present disclosure provides a humidification device and a humidification system.

A first aspect of the present disclosure relates to a humidification device, which includes a desorption structure, where the desorption structure includes a first housing, a heating layer and a desorption metal organic framework (MOF) portion;

the first housing is provided with an air inlet and an air outlet;

the heating layer is arranged in an inner side of the first housing;

the desorption MOF portion is arranged inside the first housing and attached to the heating layer, where a temperature of the desorption MOF portion is adjusted based on a temperature of the heating layer, and the desorption MOF portion is of a preset moisture.

In a possible implementation, the humidification device further includes an absorption structure, the absorption structure including a second housing and an absorption MOF portion arranged inside the second housing;

where the second housing is configured to enable the absorption MOF portion to acquire water from surrounding environment.

In a possible implementation, where the second housing is provided with a plurality of through holes for contacting with the surrounding environment.

In a possible implementation, where a first chamber and a second chamber are arranged inside the second housing, the first chamber and the second chamber are separated by a wall;

the absorption MOF portion includes a first MOF sub-portion and a second MOF sub-portion, the first MOF sub-portion is arranged in the first chamber, and the second MOF sub-portion is arranged in the second chamber.

In a possible implementation, where the heating layer is embedded with a plurality of temperature sensors.

In a possible implementation, the humidification device further includes a controlling component;

the controlling component is connected to the first housing in an electronic manner and is configured to control a temperature of the heating layer according to a preset temperature.

In a possible implementation, where the heating layer is filled with silicone heating pad.

In a possible implementation, where the desorption MOF portion is detachable from the heating layer.

In a possible implementation, the humidification device further includes a detecting component;

the detecting component is connected to the desorption MOF portion and is configured to detect a moisture of the desorption MOF portion.

A second aspect of the present disclosure relates to a humidification system, including a humidification device according to the first aspect per se or any implementation thereof and a controlling device;

the controlling device is connected to the first housing in an electronic manner and is configured to control a temperature of the heating layer according to a preset temperature.

A third aspect of the present disclosure relates to a self-sufficient humidification device, comprising a material and a heater, where the material provides water to humidify air supplied to a patient, and the heater is configured to heat air to a desired temperature to the patient;

a heated breathing circuit with one end connected to an air outlet of the device and the other end connected to a nasal cannula which connects to the patient;

the material absorbs water from air and desorbs water in a controlled manner.

A fourth aspect of the present disclosure relates to a humidification method, including the following steps;

the first step is to provide air going from an inlet to an outlet;

the second step is to have a material with absorbed water attaching to a heater, wherein the heater desorbs water from the material;

the third step is to control a temperature of the air so that the air has a certain temperature when reaching a patient.

A fifth aspect of the present disclosure relates to a humidification method, including the following steps;

the first step is to provide air going from an inlet to an outlet;

the second step is to have a first material with absorbed water attaching to a heater, wherein the heater desorbs water from the first material;

the third step is to have a second material in a separate chamber where the second material is absorbing water from the environment;

the fourth step is to swap the first material with the second material in a controlled manner to ensure a desired humidity level can always be achieved.

DESCRIPTION OF EMBODIMENTS

Figure 1:
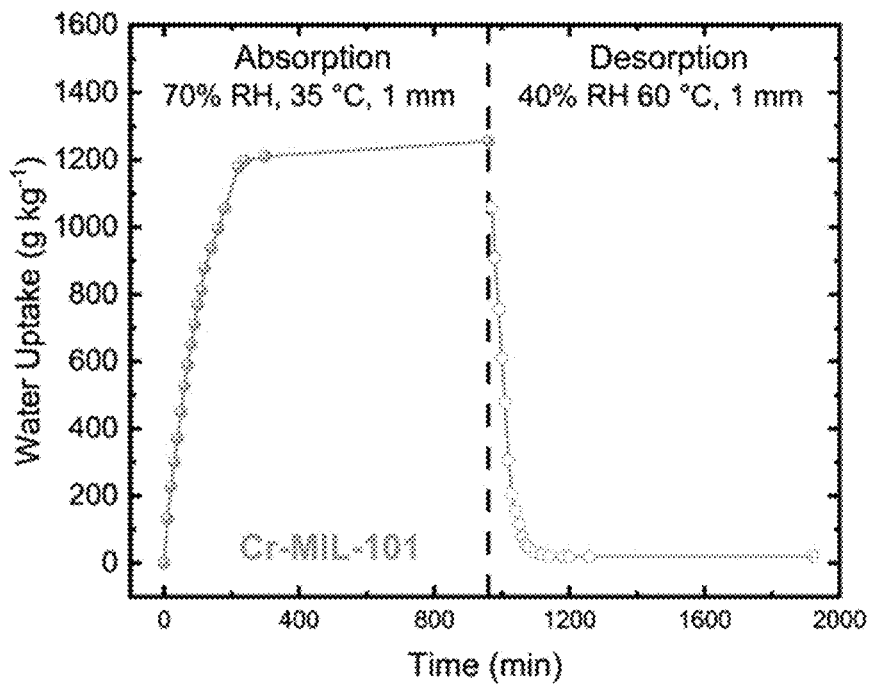
FIG. 1 illustrates the dynamic response of water vapor absorption and desorption when a MOF material Cr-MIL-101 is tested with a packing density of 0.65 at 1 mm thickness.

In the following description, reference is made to the accompanying figures, which form part of the disclosure, and which show, by way of illustration, specific aspects of embodiments of the present disclosure or specific aspects in which embodiments of the present disclosure may be used. It is understood that embodiments of the present disclosure may be used in other aspects and comprise structural or logical changes not depicted in the figures. The following detailed description, therefore, is not to be taken in a limiting sense, and the scope of the present disclosure is defined by the appended claims.

For instance, it is understood that a disclosure in connection with a described method may also hold true for a corresponding device or system configured to perform the method and vice versa. For example, if one or a plurality of specific method steps are described, a corresponding device may include one or a plurality of units, e.g. functional units, to perform the described one or plurality of method steps (e.g. one unit performing the one or plurality of steps, or a plurality of units each performing one or more of the plurality of steps), even if such one or more units are not explicitly described or illustrated in the figures. On the other hand, for example, if a specific apparatus is described based on one or a plurality of units, e.g. functional units, a corresponding method may include one step to perform the functionality of the one or plurality of units (e.g. one step performing the functionality of the one or plurality of units, or a plurality of steps each performing the functionality of one or more of the plurality of units), even if such one or plurality of steps are not explicitly described or illustrated in the figures. Further, it is understood that the features of the various exemplary embodiments and/or aspects described herein may be combined with each other, unless specifically noted otherwise.

In the embodiments of the present disclosure, expressions such as "exemplary" or "for example" are used to indicate illustration of an example or an instance. In the embodiments of the present disclosure, any embodiment or design scheme described as "exemplary" or "for example" should not be interpreted as preferred or advantageous over other embodiments or design schemes. In particular, the use of "exemplary" or "for example" is aimed at presenting related concepts in a specific manner.

As described in the background, in related art, respiratory humidification is a crucial element of the artificial respiratory system.

Respiratory humidification is a method of artificial warming and humidifying of respiratory gas for medical respiratory treatment devices. Respiratory humidification is critical part of the artificial respiratory conditioning process. Respiratory conditioning includes three essential functions, namely warming, humidification and purification of respiratory gas. Failure of respiratory humidification may result in pulmonic infections and damage to lung tissue.

In a healthy person's respiratory system, 75% of respiratory gas conditioning takes place in the upper respiratory tract, nasopharynx. The remaining 25% are achieved by the trachea. The upper respiratory tract warms, humidifies and cleanses 1,000 to 21,000 liters of respiratory gas daily, depending on body size and physical capability. Well-vascularized mucous membranes inside the nose and mouth release moisture to the passing respiratory gas. As a result, a healthy adult person evaporates 200 to 300 ml of water per day.

The respiratory humidity is a key factor for respiratory humidification, it is found that the respiratory humidity should be maintained at a proper level to ensure the therapeutic effect. High humidity and low humidity would lead to harmful effects.

On the one hand, low humidity levels can trigger or worsen symptoms of COPD. Cold and dry air can cause bronchospasm, whereas the respiratory airway narrows. The consequences are painfully inflamed nasal and oral mucous membranes as well as blockage of air passages and congestion of secretion. Cold and dry respiratory gas causes mucus on the respiratory epithelium to become more viscous, within a short time impairing the functionality of the cilia. The stroke frequency of the cilia slows down to final suspension (at <30% water vapor saturation after 3-5 minutes). After no more than one hour, damages are detectable in the cell smear. The consequences may be severe. Proper respiratory humidification is a crucial factor to effective treatment of the clinical symptoms using artificial respiratory devices. In particular, respiratory humidification is essential to avoid dry out of the upper respiratory tracts and undesirable clinical consequences, such as impairment of the ciliary function through viscous mucus and swelling mucous membranes, increase in airway resistance and decrease of compliance through increasing secretion as well as incrustation, risk of atelectases formation due to reduced surfactant activity, aggravation of gas exchange in the lung, and increased susceptibility to pulmonic infections.

On the other hand, high humidity levels may sometimes contribute to exacerbated COPD symptoms such as COPD flare-ups. Symptoms of a COPD flare-up can include more wheezing than usual, increased mucus production, persistent coughing, and severe shortness of breath. High humidity levels may exacerbate symptoms for a variety of reasons. The body must work harder to breathe when humidity levels are high, especially when the air is hot. Humid air is dense due to high water content. This density can increase airway resistance in the body. As a result, breathing may require more effort, which can worsen COPD symptoms, including shortness of breath and fatigue. Humid, hot breathing air also requires the body to work harder to stay cool. Extra work is related to more energy expense, which in turn requires more oxygen, and contribute to breathlessness.

Therefore, there is a need to realize precise control of the respiratory humidity. In an artificial respiratory system, respiratory gas needs to be conditioned before entering the human airway in order to avoid additional conditioning burden to the human respiratory system. It is desirable to control the humidity level of the air of the artificial respiratory system with precision, since too much or too little humidity of inspired air can both can damage human airway and cause clinical complications. However, the precision control of humidity of the artificial respiratory system is a very challenging task.

There are several kinds of traditional humidifiers in respiratory systems. Humidifiers are devices that add molecules of water to gas. Humidifiers act by allowing air passage inside a heated water reservoir. A humidifier is placed in the inspiratory limb of the artificial respiratory system circuit, proximal to the ventilator. After the air is loaded with water vapor in the reservoir, it travels along the inspiratory limb to the patient's airway. There are four types of humidifiers, bubble, Passover, counter-flow, and inline vaporizer. In bubble humidifiers, gas is forced down a tube into the bottom of a water container. The gas escapes from the distal end of the tube under water surface forming bubbles, which gain humidity as they rise to the water surface. In a passover humidifier, gas passes over the surface of a heated water reservoir carrying water vapor to the patient. It is typically used for the purpose of invasive and noninvasive mechanical ventilation. In different designs, Wick or hydrophobic membranes are used to achieve lower flow resistance and reduce micro aerosols in the process. In a counterflow humidifier, heated water and gas travel in counter direction in a large surface area porous material to achieve the purpose of humidification. Inline vaporizer uses a small plastic capsule to inject water vapor into the gas in the inspiratory limb of the ventilator circuit immediately proximal to the patient wye. These devices involve the use of liquid water reservoir that hampers the portability applications.

Another frequently used device is an HME, i.e., a heat and moister exchanger. Heat and moisture exchangers are also called artificial noses because they mimic the action of nasal cavity in gas humidification.

However, the portability of the conventional humidifier using a water container is relatively low, besides, these kinds of humidifiers cost high since the energy consumption for heating of the water is relatively high. Some existing humidifiers use moist sponges which have high water-absorbing capabilities for humidification, however, such kinds of humidifiers cannot even satisfy the lowest requirements for respiratory care humidification, for example, 12 mg/liter according to ISO 80601-2-74:2017: 201.12.1.101 standard.

In sum, none of these devices simultaneously possess the properties of precision control, ease of use, high capacity, portability and low cost. Hence, the present disclosure focuses on providing a humidifier which could realize precise control on the humidity of the air.

In order to solve the above technical problems, the inventor has analyzed multiple kinds of materials for achieving the humidification effect, and finally paid attention to the metal-organic frameworks (MOF).

In recent years, reticular chemistry links molecular building units through strong bonds to make crystalline, extended structures such as MOFs. MOFs were proven to have permanent porosity. A unique feature of MOFs is that they have pores without walls, and therefore their internal surface area can be as large as 10,000 m2/g. Despite the emptiness, MOFs are architecturally, mechanically, chemically, and thermally stable. The porous and stable properties of MOFS make them attractive for gas capture, gas desorption, gas separation, and storage applications.

Metal-organic frameworks (MOFs) due to their unique micro-structure, intrinsic porosity, and unprecedented functional and chemical control have a high potential to be used for harvesting water from air. It has been found that Zr-MOF-808 can produce up to 8.66 LH2O kg-1MOF day-1. It has also been reported that MOF can hold up to 2 times as much water as its body weight. By changing the air pressure and temperature, the desorption process can be initiated and precisely controlled.

The unique features of MOF for water harvesting, water desorption, and water storage are the basis of the present disclosure.

In the present disclosure, a novel humidification system for respiratory therapy is presented. This humidification system incorporates a MOF (Metal Organic Frameworks structure. The MOF structure stores water on the surface of the MOF. Air passes through the MOF structure and extract the water from the surface of the MOF.

Using MOF to store water is advantageous vs. liquid water reservoir. Liquid water reservoir is prone to spill and leak. Liquid water reservoir also has rigid orientation requirement. MOF structure anchors water on the surface of MOF structure, hence de-mobilize the water molecules, enabling easy operation and portability.

This embodiment of the present disclosure enables a humidifier with no extra liquid water supply. It is a highly efficient system with light weight and portability. Liquid water needs water source. MOF structure makes the humidification system self-sufficient and makes portable system practical.

Incorporation of the high surface area MOF in such systems enables smaller size, lower weight, and higher flow oxygen therapy treatment in the home treatment setting. The present disclosure also enables light weight, small size oxygen treatment for mobile use cases.

The absorption and desorption attributes of one kind of MOF are shown in FIG. 1, where it illustrates the dynamic response of water vapor absorption and desorption when a MOF material Cr-MIL-101 is tested with a packing density of 0.65 at 1 mm thickness. Taking advantage of the shown characteristics of MOF, water vapor can be released from the MOF material precisely by controlling its temperature.

An embodiment of the present disclosure provides an MOF based humidification system.

The major components of the humidification system include a desorption chamber with air inlet and outlet ports, a heater layer (e.g., silicone heating pad as the heating element) attached to the inner wall of desorption chamber with embedded temperature sensors, and a layer made of MOF material that holds water. The heater layer is fixed to the chamber's inner wall, while the MOF layer part is detachable. When water is running out in the MOF layer, it can be interchanged by another one that has abundant water.

Figure 2:
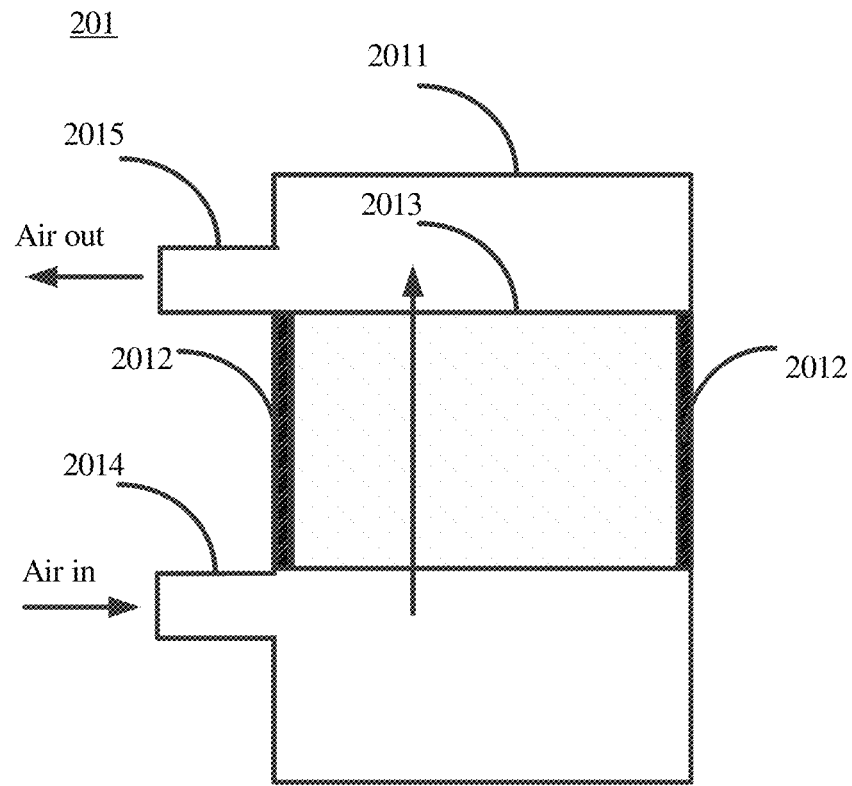
FIG. 2 shows a schematic structural diagram of a humidification device provided by an embodiment of the present disclosure.

FIG. 2 show a schematic structural diagram of a humidifier provided by an embodiment of the present disclosure.

As shown in FIG. 2, the humidification device includes a desorption structure 201, where the desorption structure 201 includes a first housing 2011, a heating layer 2012 and a desorption metal organic framework (MOF) portion 2013;

the first housing 2011 is provided with an air inlet 2014 and an air outlet 2015;

the heating layer 2012 is arranged in an inner side of the first housing 2011;

the desorption MOF portion 2013 is arranged inside the first housing 2011 and attached to the heating layer 2012, where a temperature of the desorption MOF portion 2013 is adjusted based on a temperature of the heating layer, and the desorption MOF portion is of a preset moisture.

As shown in FIG. 2, the first housing 2011 forms a chamber and the heating layer 2012 and the desorption MOF portion 2013 are arranged in the chamber.

The pathway of the air is shown with arrows. Dry air may go inside the desorption structure 201 of the humidification device via the air inlet 2014, and then pass through the desorption MOF portion 2013, and finally go out of the desorption structure 201 via the air outlet 2015. By controlling the temperature of the heating layer, the temperature of the desorption MOF portion 2013 can be maintained at a preset temperature, combining FIG. 1 and related description, it is thus clear that the humidity of the air passing through the desorption MOF portion 2013 can thus be controlled precisely.

In an implementation, the heating layer is embedded with a plurality of temperature sensors. The sensors may be used to detect the temperature of the heating layer, thus facilitating the adjustment of the temperature of the MOF portion. The number of the sensors and the specific positions of the sensors may be designed according to actual needs.

In an implementation, the humidification device further includes a controlling component;

the controlling component may be connected to the first housing in an electronic manner and is configured to control a temperature of the heating layer according to a preset temperature.

In an implementation, the heating layer is filled with silicone heating pad.

In an implementation, the desorption MOF portion is detachable from the heating layer.

Besides, the desorption MOF portion is of a preset moisture, so as to ensure the normal operation of the humidification device, since if the desorption MOF portion is in a relatively dry state, it can no longer work normally, that is, to humidify the air passing by. Therefore, in an implementation, for example, the humidification device further includes a detecting component, the detecting component is connected to the desorption MOF portion and is configured to detect a moisture of the desorption MOF portion.

According to the solution provided by the present disclosure, since the temperature of the desorption MOF portion can be adjusted based on the temperature of the heating layer, the humidity of the desorption MOF portion can thus be adjusted appropriately. In this way, when using the humidification device, the humidity of the output air can thus be regarded as being approximately equivalent to the humidity of the desorption MOF portion, thereby achieving precise control on the humidity of the air.

Thanks to the rigidity of the MOF material, the humidification device can thus be of a high portability and a small volume.

In addition to the desorption capability, the humidification device can also be provided with an absorption structure, so as to "charge" the MOF portion therein. Here the term "charge" may be understood as reloading water to the MOF portion, so that the dry MOF material can be restored to a moist state, and the MOF portion can be reused for humidification again. The absorption structure is place in a separate chamber.

A control method is adopted to determine when to swap the material in the desorption structure and the one in the absorption structure. In a preferred embodiment, the determination is based on the level of water in the desorption structure. When the water in desorption structure is low, the two materials are swapped to ensure to a desired humidity level can always be achieved.

An embodiment of the present disclosure provides the absorption structure (absorption chamber) for water refill of MOF layers (MOF layer 1 and MOF layer 2). The dry MOF layer can be placed in the absorption structure to reload water by capturing water vapor from the environment around it. More than one MOF layers can be placed in the absorption structure. Through holes on the chamber wall (used for separating the upper absorption chamber and the lower absorption chamber) and chamber cap allow air with moisture gets into the chamber. MOF layers inside the chambers will capture the water vapor and hold the water with their porous and crystalline. It may take a couple hours before the MOF layer is refilled with adequate water and ready to be used in the humidification device described by FIG. 2.

Figure 3A:
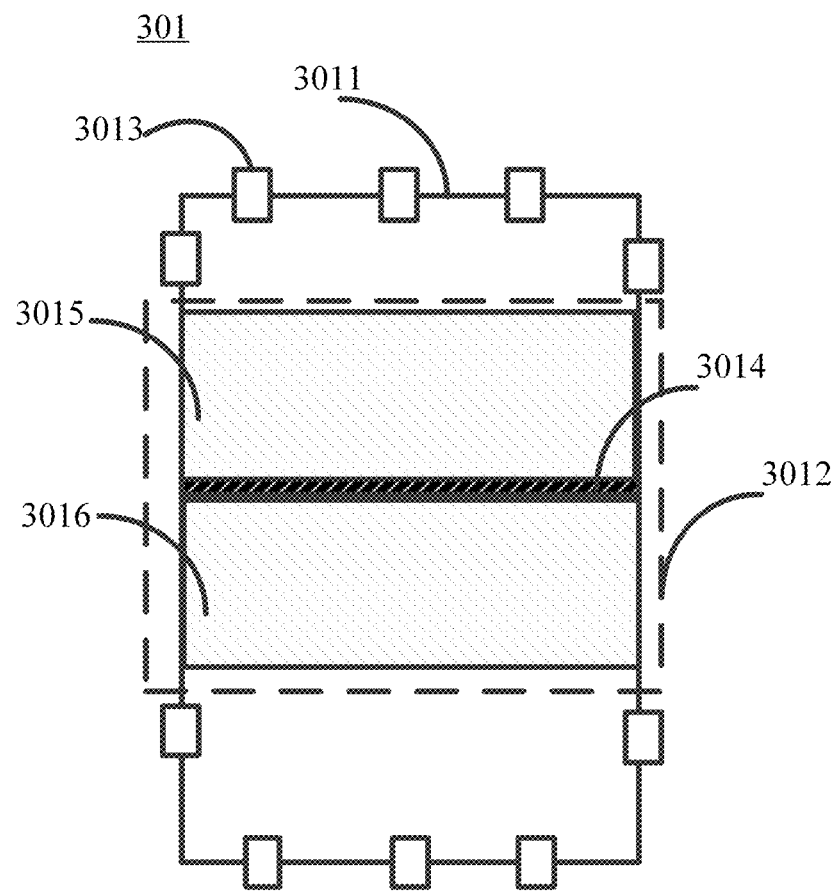
FIG. 3a shows a schematic structural diagram of a humidification device provided by an embodiment of the present disclosure.

As shown in FIG. 3*a*, the humidification device further includes an absorption structure 301, the absorption structure 301 includes a second housing 3011 and an absorption MOF portion 3012 arranged inside the second housing 3011;

where the second housing 3011 is configured to enable the absorption MOF portion 3012 to acquire water from surrounding environment.

In an implementation, the second housing 3011 is provided with a plurality of through holes 3013 for contacting with the surrounding environment (air for example). Here the size and the number of the holes is not limited in the present disclosure, which should be adjusted according to actual needs. In another possible implementation, the second housing may have a sealed structure, instead of absorbing water from the air, some water may be stored in advance inside the chamber formed by the second housing, and the MOF portion in the second housing may finish the "charging" (absorption) with the aide of the water.

In an implementation, a first chamber and a second chamber (not shown) are arranged inside the second housing 3011, the first chamber and the second chamber are separated by a wall 3014;

the absorption MOF portion 3012 includes a first MOF sub-portion 3015 and a second MOF sub-portion 3016, the first MOF sub-portion 3015 is arranged in the first chamber, and the second MOF sub-portion 3016 is arranged in the second chamber.

In another embodiment of the present disclosure, two MOF structures are used. While one MOF structure is used for humidification as described above, another MOF structure is used to harvest water from the ambient environment. According to this setting, one as a standby MOF portion and the other as the "charging" one, it is ensured that there is always one MOF portion ready for use. Of course, there could be multiple standby MOF portions and the structure of the humidification device would change accordingly. The more the MOF portions, the stronger the ability of the humidification device becomes.

The first chamber and the second chamber are not shown in the figure, they may are respective spaces used for accommodating the first and second MOF sub-sections, and may be formed using shells.

Similar to FIG. 3*a*, through holes on the housing allow air with moisture gets into the housing. MOF portions (layers) inside the chamber will capture the water vapor and hold the water with their porous and crystalline. It may take a couple hours before the MOF portion (layer) is refilled with adequate water and ready to be used in the humidification device described by FIG. 2.

It should be noted that, although the desorption structure 201 shown in FIG. 2 is of a rectangle shape, the shape of the housing of the desorption structure is not limited in the present disclosure, in fact, various designs may be possible depending on actual requirements. Similarly, the same applies for the shape shown in FIG. 3*a*.

The desorption structure and the absorption portion can be set in the same humidification device, or may be set separately on two device, which is not limited in the present disclosure.

Figure 3B:
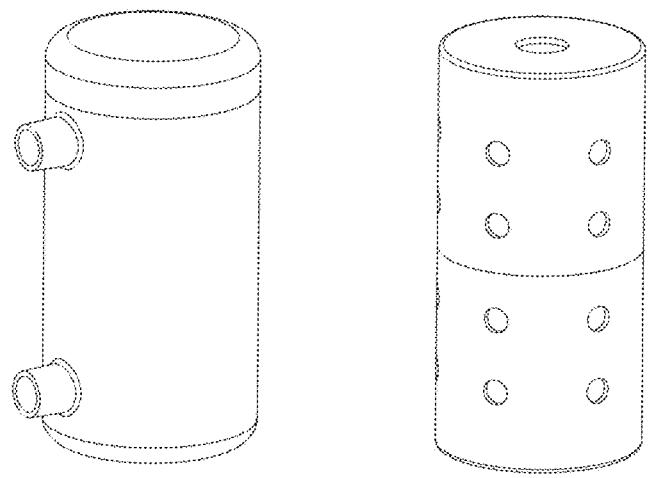
FIG. 3b shows exemplary desorption and absorption chambers provided by an embodiment of the present disclosure.

Besides, all sizes, positions and the number of the components shown in the figures are all for illustrative purpose. Any other designs are also possible. For example, FIG. 3b shows exemplary desorption and absorption chambers provided by an embodiment of the present disclosure. Here the desorption chamber on the left may be used for desorption, which could be a possible implementation of the desorption structure shown in FIG. 2, and the absorption chamber on the right may be used for desorption, which could be a possible implementation of the absorption structure shown in FIG. 3a. It is worth noting that the number of the holes, the shape of the air inlet and the air outlet, the shape of the chambers are simply for illustrative purpose, which are not limited in the present disclosure.

The present disclosure also provides a humidification system, includes a humidification device according to any of the above embodiments and a controlling device;

the controlling device is connected to the first housing in an electronic manner and is configured to control a temperature of the heating layer according to a preset temperature.

In addition to the humidity consideration, the inventor also notices that the temperature of the air output by the humidifiers is also a critical factor that may affect the clinical outcome and user experience. For example, normally a temperature of 37 degrees Celsius, which is approximate to the body temperature, may be suitable for a patient. Hence, in an implementation, the present disclosure also provides a humidifier whose output air is at a proper temperature. The control of the temperature may be realized at the humidification device, or by virtue of the heating element arranged between the humidification device and the respiratory pipe, also called breathing circuit, with a nasal cannula connecting between the device and the patient's nose.

Figure 4:
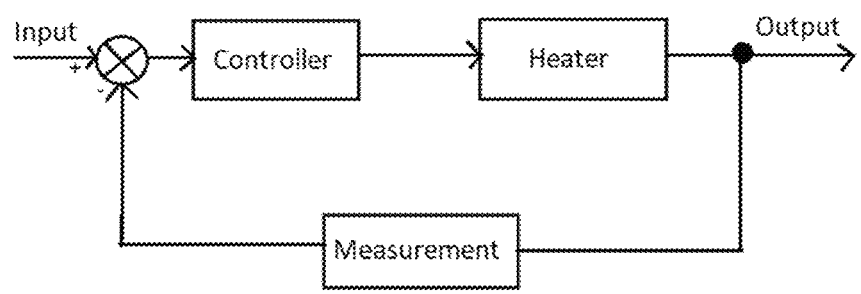
FIG. 4 is a feedback control system for temperature control of a desorption structure.

The present disclosure also provides a method for controlling the humidity of the air passing by the humidification device. As shown in FIG. 4, a feedback control system is utilized for controlling the temperature of the desorption structure to desired levels, such that accurate water vapor release from the MOF layer can be achieved. Input: desired temperature level or profile. The output of the controlling system may be the temperature of the desorption structure (for example, the desorption structure 201), and the controller may be PID or of other types, it may correspond to the controlling component or the controlling device in the above embodiments. The heater (corresponding to the heating layer 2012 in FIG. 2) may convert an electric current to heat, e.g., silicone heating pad. The measurement here may refer to a sensing and signal conditioning system for temperature measurement.

In such a system, the heating element (heater in FIG. 4) is powered by an embedded battery, and multiple temperature sensors are placed in different locations to give temperature measurements that are used to calculate the feedback for the temperature controller (controller in FIG. 4). In a possible implementation, a PID controller with gain scheduling for different operating conditions (referred to as a gain-scheduled PID controller) may be adopted to implement the control method. Alternatively, a model-based control approach can be used, in which a mathematical model of the heated desorption chamber system is developed and incorporated into the controller. The model-based controller incorporates knowledge of the system dynamics for temperature change in the desorption chamber. It is expected to have significantly better performance than a gain-scheduled PID controller.

An embodiment of the present disclosure relates to a humidification method, including the following steps;

the first step is to provide air going from an inlet to an outlet;

the second step is to have a material with absorbed water attaching to a heater, wherein the heater desorbs water from the material;

the third step is to control a temperature of the air so that the air has a certain temperature when reaching a patient.

An embodiment of the present disclosure relates to a humidification method, including the following steps;

the first step is to provide air going from an inlet to an outlet;

the second step is to have a first material with absorbed water attaching to a heater, wherein the heater desorbs water from the first material;

the third step is to have a second material in a separate chamber where the second material is absorbing water from the environment;

the fourth step is to swap the first material with the second material in a controlled manner to ensure a desired humidity level can always be achieved.

Terms such as "first", "second" and the like in the specification and claims of the present disclosure as well as in the above drawings are intended to distinguish different objects, but not intended to define a particular order.

The term "a" or "an" is not intended to specify one or a single element, instead, it may be used to represent a plurality of elements where appropriate.

In one or more examples, the functions described may be implemented in hardware, software, firmware, or any combination thereof. For example, the functions may be implemented by one or more processors, such as one or more application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, the techniques could be fully implemented in one or more circuits or logic elements.

In the claims, the word "including" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate, preclude or suggest that a combination of these measures cannot be used to advantage.

The foregoing detailed description has been presented for purposes of illustration and description. It is not intended to be exhaustive or to limit the subject matter claimed herein to the precise form(s) disclosed. Many modifications and variations are possible in light of the above teachings. The described embodiments were chosen in order to best explain the principles of the disclosed technology and its practical application to thereby enable others skilled in the art to best utilize the technology in various embodiments and with various modifications as are suited to the particular use contemplated. Those embodiments with various modifications are within the range and scope of the following claims.

What is claimed is:

1. A humidification device, comprising:
a desorption structure, wherein the desorption structure comprises:
a first housing,
a heating layer and
a desorption metal organic framework (MOF) portion; the first housing is provided with an air inlet and an air outlet; the heating layer is arranged in an inner side of the first housing; and the desorption MOF portion is arranged inside the first housing and detachably attached to the heating layer, wherein a temperature of the desorption MOF portion is adjusted based on a temperature of the heating layer, and the desorption MOF portion is of a preset moisture;
the humidification device further comprises an absorption structure, the absorption structure comprising a second housing and an absorption MOF portion arranged inside the second housing;
wherein the second housing is provided with a plurality of through holes for contacting with air outside the second housing, so as to enable the absorption MOF portion to acquire water from the air outside the second housing by virtue of the plurality of through holes; and
the humidification device further comprising a detecting component; the detecting component is connected to the desorption MOF portion and is configured to detect whether a moisture of the desorption MOF portion is lower than a preset moisture level, wherein the preset moisture level represents a critical moisture level that the desorption MOF portion needs to be swapped with the absorption MOF portion.

2. The humidification device according to claim 1, wherein a first chamber and a second chamber are arranged inside the second housing, the first chamber and the second chamber are separated by a wall; and the absorption MOF portion comprises a first MOF sub-portion and a second MOF sub-portion, the first MOF sub-portion is arranged in the first chamber, and the second MOF sub-portion is arranged in the second chamber.

3. The humidification device according to claim 1, wherein the heating layer is embedded with a plurality of temperature sensors.

4. The humidification device according to claim 1, further comprising a controlling component; and the controlling component is connected to the first housing in an electronic manner and is configured to control a temperature of the heating layer according to a preset temperature.

5. The humidification device according to claim 1, wherein the heating layer is filled with silicone heating pad.

6. A humidification system, comprising a humidification device according to claim 1 and a controlling device; the controlling device is connected to the first housing in an electronic manner and is configured to control a temperature of the heating layer according to a preset temperature.

7. The humidification system according to claim 6, wherein the controlling device is a gain-scheduled proportional integral derivative (PID) controller.

8. The humidification system according to claim 6, wherein the controlling device is a model-based controller.

* * * * *